United States Patent [19]

Seubert et al.

[11] Patent Number: 5,486,538
[45] Date of Patent: Jan. 23, 1996

[54] PRECIOUS METAL HUMATES AND THEIR PREPARATIONS

[75] Inventors: Bernhard Seubert, Edingen-Neckarhausen; Anton F. Haase, Muhltal, both of Germany

[73] Assignee: Rutgerswerke Aktiengesellschaft, Germany

[21] Appl. No.: 298,419

[22] Filed: Aug. 29, 1994

[30] Foreign Application Priority Data

Oct. 16, 1993 [DE] Germany ............... 43 35 370.3

[51] Int. Cl.⁶ ............. A61K 31/28; C07F 1/12; C07F 15/00
[52] U.S. Cl. ............. 514/492; 514/495; 556/2; 556/114; 556/136
[58] Field of Search ............. 556/136, 114, 556/2; 514/492, 495

[56] References Cited

U.S. PATENT DOCUMENTS 3,586,622  6/1971  Thompson et al. .............. 208/204
5,284,651  2/1994  Riede et al. .............. 424/78.06
5,360,915  11/1994  Riede et al. .............. 549/200

FOREIGN PATENT DOCUMENTS 0281678  9/1988  European Pat. Off. .
0531866  3/1993  European Pat. Off. .

OTHER PUBLICATIONS

Copy of European Search Report (1 page) 1995.

Chemical Abstracts, vol. 118, Abstract No. 106459b, (1993).

Primary Examiner—Porfirio Nazario-Gonzalez
Attorney, Agent, or Firm—Bierman and Muserlian

[57] ABSTRACT

A precious metal salt of a low molecular humic acid containing 1 to 5% by weight of the precious metal processes for their preparation and a method of stabilizing alkali metal humate and their medical uses.

5 Claims, No Drawings

PRECIOUS METAL HUMATES AND THEIR PREPARATIONS

STATE OF THE ART

Precious metal compounds and their preparations are used in various fields of medicine. Silver acts as a wide spectrum biocide, as a wound treatment agent for burns, and as a scab former while gold is used in the therapy of rheumatoid diseases. Platinum is used in the form of cis-platinum in the treatment of malignant tumors. The proven effects of precious metal compounds are countered due to high toxicity and by strong side effects which restrict the therapeutic spectrum.

However, it is known from DE-A 41 29 872 that humic acid-metal compounds are physiologically well tolerated and are being used also in the medical field. It was to be expected that also the medical applicability of precious metal compounds would be improved when the precious metals are present and used in the form of compounds with humic acid, particularly humic acid of low molecular weight. Unfortunately, it was found that by conventional production methods such as addition of a metal salt solution to aqueous humic acid solutions or to partially neutralized alkaline humate solutions, stable humates can not be produced with precious metal salts. The respective products or complexes decompose after a short time and eliminate the precious metals which is in agreement with observations of other specialists. Thus, it is known from Chem. Geol., Vol. 102 (1–4)), pp. 53–71 (C.A. 118(12: 106459b) that under all observed conditions, gold(III) chloride is reduced by humins to elementary colloidal gold within 8 to 14 days.

OBJECTS OF THE INVENTION

It is an object of the invention to provide stable precious metal salts of low molecular weight humates and novel processes for their preparations.

It is another object of the invention to provide novel therapeutic compositions for the treatment of malignant tumors, rheumatic diseases and wide-spectrum biocides and to a novel method of stabilizing alkali metal humate preparations.

These and other objects and advantages of the invention will become obvious from the following detailed description.

THE INVENTION

One process of the invention for the preparation of a stable precious metal humate comprises electrochemically oxidizing an aqueous alkaline solution of a polyvalent phenolic compound in an anode chamber, adding to the said solution after the start of the oxidation reaction an aqueous solution or hydrosol of the precious metal salt, completing the electrochemical oxidation and adjusting the pH to 4 to 6 to obtain the precious metal humate.

A second process of the invention for the preparation of a stable precious metal humate comprises plasmachemically oxidizing an aqueous alkaline solution of a polyvalent phenolic compound in a reaction tube, adding to the solution after the start of the oxidation reaction an aqueous solution or hydrosol of the precious metal salt, completing the oxidation reaction and adjusting the pH to 4 to 6 to obtain the precious metal humate.

The precious metal salts of a humic acid with a mean molecular weight of 900 to 30,000 Daltons containing 1 to 5% by weight of the precious metal of the invention are suitable particularly as stabilizers for aqueous alkali metal humate preparations, silver humate as a wide-spectrum biocide, gold humate for the therapy of rheumatic diseases, and platinum humate for the treatment of malignant tumors.

While the reaction of precious metal compounds with humic acid or humates does not lead to the stable inclusion of the precious metal component, the durable incorporation of the precious metal component is possible in certain synthetic processes of humates, namely in the electrochemical and plasmachemical oxidation of alkaline aqueous solutions of polyvalent phenolic compounds when a solution or a hydrosol of a precious metal salt is added to the solution of the polyvalent phenolic compound(s) in an anodic compartment or reaction chamber at the beginning of the oxidation reaction.

In these synthetic processes, stable compounds of the freshly synthesized humic acids with precious metals are formed as precious metal humates. Up to a precious metal content of 5% by weight, these humates are stable in aqueous solution at room temperature for more than half a year. Even in a short-time stability test at a 24-hour temperature of 90° C., these solutions shown no alteration.

The electrochemical and the plasmachemical oxidation of polyvalent phenolic compounds for the production of low molecular weight alkali metal humates is known from EP-B 0281678, DE-A 41 34 379 and DE-A 41 34 384. The process variants and products there described can be used also to produce the precious metal humates of the invention. However, the synthesis by chemical oxidation of polyvalent phenolic compounds also disclosed in these documents is not suitable for the production of stable precious metal humates.

Examples of starting products for the process of the invention are all common polyvalent phenols such as pyrocatechin, resorcinol, hydroquinone, orcinol, gallic acid, protocatechuic acid, pyrogallol, 2-oxyhydroquinone, phloroglu, or tetraoxybenzols.

Other useful polyvalent phenolic compounds are those of the formula

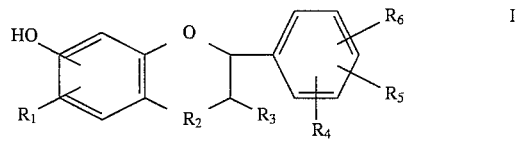

or

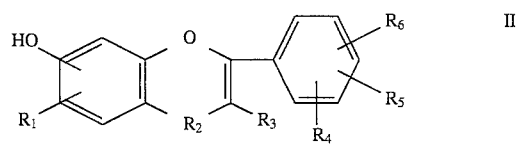

wherein $R_1$, $R_3$ and $R_4$ are individually —OH or hydrogen, $R_2$ is —CO— or —CH$_2$—, and $R_5$ and $R_6$ are individually hydrogen, —OH or methoxy, with the proviso that $R_4$, $R_5$ and $R_6$ are not all hydrogen.

Examples for such compounds are Narigenin, Eriodictyol, Hesperitin, Pelargonidin, Cyanidin, Delphinidin, Peonidin, Syringidin, Catechin or Epicatechin, Gallocatechin, Apigenin, Fisetin, Robinetin, Gossypetin, Luteolin, Camphorol, Quercetin, and Morin or Myricetin. Preferred building blocks are quercetin and catechin. The polyvalent phenols can be used as pure substances or in mixture with one another. They are used as 1 to 5% by weight aqueous solutions.

Examples of precious metal components are all water-soluble salts in the form of aqueous solutions or hydrosols of the precious metals selected from the group consisting of gold, silver, mercury, rhenium as well as of the platinum metals ruthenium, rhodium, palladium, osmium, iridium and platinum. The hydrosols are commercial products containing colloidal precious metal with a protective colloid, usually gum arabic.

For the reaction, the polyvalent phenols are dissolved in an alkaline aqueous solution. As bases, all alkali metal hydroxides, ammonia, or strong amines in aqueous solution can be used. For economical reasons, sodium and potassium hydroxide are preferred.

For the production of humates with a mean molecular weight of 1000 D with a scatter range of 300 to 1500 D, the employed alkali metal amount will be, according to the teaching of EP-B 0,281,678, in the range of 1.2 to 1.6 times the stoichiometric amount necessary for phenolate formation of the polyvalent phenols, that is, for the neutralization of all phenolic OH groups. A pH value of the reaction solution of 8 to 9 then adjusts itself.

During the subsequent oxidation there occurs, also in the presence of precious metal compounds, an automatic limitation of the reaction for products having mean molecular weight of 1000 D with a scatter range of 300 to 1500 D.

For the production of physiologically active, non-mutagenic humates of a molecular weight of about 50,000 D, corresponding to DE-A 41 34 379, the alkali metal amount is adjusted so that during the oxidation, the pH value of the reaction medium is in the range of pH 8.5 to 11. The current supply is proportioned so that the content of the quinones corresponding to the polyvalent phenols is always less than 0.5%, referred to the polyvalent phenols, and that the oxidation reaction is stopped when the quinone concentration decreases despite current supply, or respectively when the quinone concentration has dropped below 0.05%, referred to the polyvalent phenols used, despite current supply.

The electrochemical oxidation occurs in an electrochemical reactor with the oxidation rate being determined by adjusting the anodic voltage and the current density. The anodic voltage can be varied in the range of 1 to 20 V, and the current density in the range of 0.5 to 4 A/cm$^2$.

The plasmachemical oxidation takes place in an apparatus known per se for corona discharge with the oxidation rate being determined by adjustment of the operating voltage and of the field strength. The voltage may be varied in the range of 20 to 250 kV at frequencies of 16⅔ to 400 Hz, and the field strength from 2 to 80, preferably 10 to 20 kV/cm. The pressure inside the discharge apparatus is 0.05 to 3 kPa. Operation is possible with oxygen as well as with air.

Both the electrochemical and the plasmachemical oxidation are conducted in the temperature range of 15° to 55° C., preferably 30° to 50° C. The temperature of the plasma is 150° to 300° C.

Immediately after the start of the oxidation reaction which is when the reaction mixture begins to become brown, in the electrochemical oxidation there is added to the reaction mixture in the anodic chamber or in the plasmachemical reaction in the reaction tube, an aqueous solution or a hydrosol of a corresponding precious metal salt in an amount such that the concentration of the precious metal in the newly formed reaction mixture is in the range of 1 to 5% by weight.

After termination of the oxidation reaction, the pH value of the reaction mixture is adjusted to a value in the range of 4 to 6, and if necessary, buffered. This is done either by addition of acid or by action of acid ion exchanger and/or subsequent addition of a corresponding buffer solution (e.g. phosphate, tris, or citric acid buffer).

If the neutralized and buffered solution contains undesirable suspended matter, this suspended matter is removed by a separating process such as centrifuging (10,000 to 30,000 xg) or filtering through a very fine-pore filter material. Although for many applications, this solution can be used directly, when the products are used as medicaments, it should be purified by purification methods known per se such as preparative chromatographic methods, ultrafiltration, ultracentrifugation or electrodialysis with undesirable by-products being removed.

There is obtained a solution which contains about 2 to 8% precious metal humates which solution can be used directly or it can be concentrated to a 20% solution by careful removal of water, for instance by freeze drying. The resulting solution and the concentrated solution are stable.

In the following examples, there are described several preferred embodiments to illustrate the invention. However, it should be understood that the invention is not intended to be limited to the specific embodiments.

EXAMPLE 1

100 g of an aqueous mixture of hydroquinone (3% w/w) were adjusted to a pH of 9 with potassium hydroxide and the mixture was placed into the anodic chamber of an electrochemical cell, the cathodic chamber being charged with an aqueous potassium hydroxide solution with a pH of 9. The cell was operated at a DC voltage of U=2.5 volts, with the pH value being kept constant by adding 1% potassium hydroxide. At the beginning of the oxidation reaction to form the humate recognizable by browning of the reaction mixture, 2 ml of an aqueous solution of silver lactate (0.14 g) were proportioned into the anodic chamber. After completion of the addition, the anodic oxidation was continued for 12 hours, and then the reaction mixture was neutralized with a suitable acid ion exchanger and adjusted to a pH of 5 to obtain a clear, brown solution which remained stable at a temperature of 90° C. for 24 hours. The silver content was 2.5%.

EXAMPLE 2

Using the procedure of Example 1, pyrogallol and silver lactate were reacted to obtain a silver humate containing 2.3% by weight of silver.

EXAMPLE 3

Using the procedure of Example 1, an aqueous solution of 2 g of hydroquinone per 100 ml and 2 ml of an aqueous solution of 0.075 g of gold tetrachloride acid trihydrate were reacted to obtain gold humate containing 1.8% by weight of gold.

EXAMPLE 4

Using the procedure of Example 1, a solution of 4 g of pyrogallol in 100 ml of water and a solution of 2 ml of water and 0.13 g of gold tetrachloride acid trihydrate were reacted to obtain gold humate containing 1.6% by weight of gold.

EXAMPLE 5

Using the procedure of Example 1, a solution of 5 g of hydroquinone in 100 ml of water and a solution of 0.18 g of hexachloroplatinum acid hydrate in 2 ml of water were reacted to obtain platinum humate containing 1.3% by weight of platinum.

EXAMPLE 6

Using the procedure of Example 1, a solution of 3.5 g of pyrogallol in 100 ml of water and a solution of 0.13 g of hexachloroplatinum acid hydrate in 2 ml of water were reacted to obtain platinum humate containing 1.4% by weight of platinum.

EXAMPLE 7

100 ml of an aqueous mixture of hydroquinone (3% w/w) adjusted to a pH of 9.5 with potassium hydroxide were placed into a low-temperature plasma tube operated with oxygen at 0.1 kPa and 15 kV/cm. The mixture traversed the discharge zone, was collected at the lower end of the tube, was again adjusted to a pH of 9.5 by adding 1% potassium hydroxide solution, and returned to the storage vessel. As soon as the oxidation reaction set in as recognizable by browning of the reaction mixture, 2 ml of an aqueous solution of 0.14 g of silver lactate were added. After completion of the addition, the reaction was continued for 5 hours. Then, the mixture was neutralized with a suitable acid ion exchanger to obtain a clear brown solution of silver humate which remained stable at a temperature of 90° C. for 24 hours. The silver content was 2.6% by weight.

EXAMPLE 8

Using the procedure of Example 7, a solution of 3.7 g of pyrogallol in 100 ml of water and a solution of 0.16 g of silver lactate in 2 ml of water were reacted to obtain silver humate containing 2.3% by weight of silver.

EXAMPLE 9

Using the procedure of Example 7, a solution of 1.5 g of hydroquinone in 100 ml of water and a solution of 0.12 g of gold tetrachloride acid trihydrate in 2 ml of water were reacted to obtain gold humate containing 1.6% by weight of gold.

EXAMPLE 10

Using the procedure of Example 7, a solution of 4.5 g of pyrogallol in 100 ml of water and a solution of 0.12 g of gold tetrachloride acid trihydrate in 2 ml of water were reacted to obtain gold humate with 1.3% by weight of gold.

EXAMPLE 11

Using the procedure of Example 7, a solution of 5 g of hydroquinone in 100 ml of water and a solution of 0.15 g of hexachloroplatinum acid hydrate in 2 ml of water were reacted to obtain platinum humate containing 1.1% by weight of platinum.

EXAMPLE 12

Using the procedure of Example 7, a solution of 2.2 g of pyrogallol in 100 ml of water and a solution of 0.08 g of hexachloroplatinum acid hydrate in 2 ml of water were reacted to obtain platinum humate containing 1.3% by weight of platinum.

Various modifications of the products and process of the invention may be made without departing from the spirit or scope thereof and it is to be understood that the invention is intended to be limited only as defined in the appended claims.

What is claimed is:

1. A process for the preparation of a stable precious metal humate comprising electrochemically oxidizing an aqueous alkaline solution of a polyvalent phenolic compound in an anode chamber, adding to the said solution after the start of the oxidation reaction an aqueous solution or hydrosol of the precious metal salt, completing the electrochemical oxidation and adjusting the pH to 4 to 6 to obtain the precious metal humate.

2. A process for the preparation of a stable precious metal humate comprising plasmachemically oxidizing an aqueous alkaline solution of a polyvalent phenolic compound in the reaction tube, adding to the solution after the start of the oxidation reaction an aqueous solution or hydrosol of the precious metal salt, completing the oxidation reaction and adjusting the pH to 4 to 6 to obtain the precious metal humate.

3. A precious metal salt of a humic acid with a mean molecular weight of 900 to 30,000 Daltons containing 1 to 5% by weight of the precious metal.

4. An aqueous alkali humate preparation stabilized with a stabilizing effective amount of the precious metal salt of claim 3.

5. The precious metal salt of claim 3 wherein the metal is selected from the group consisting of gold, ruthenium, rhodium, palladium, osmium, iridium and platinum.

* * * * *